United States Patent
Sia et al.

(10) Patent No.: US 10,631,766 B2
(45) Date of Patent: Apr. 28, 2020

(54) DEVICES AND SYSTEMS FOR OPTICALLY DETERMINING A CONCENTRATION OF AN ANALYTE IN A LIVING SUBJECT USING HYDROGEL-BASED, FLUORESCENT MICRONEEDLES AND METHODS OF MANUFACTURE THEREOF

(71) Applicant: The Trustees of Columbia University in the City of New York, New York, NY (US)

(72) Inventors: Samuel K. Sia, New York, NY (US); Matthieu Jean Michel Rueegg, Saint-Sulpice (CH); Nalin Tejavibulya, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 201 days.

(21) Appl. No.: 15/554,406

(22) PCT Filed: Mar. 4, 2016

(86) PCT No.: PCT/US2016/020936
§ 371 (c)(1),
(2) Date: Aug. 29, 2017

(87) PCT Pub. No.: WO2016/141307
PCT Pub. Date: Sep. 9, 2016

(65) Prior Publication Data
US 2018/0177439 A1    Jun. 28, 2018

Related U.S. Application Data

(60) Provisional application No. 62/128,973, filed on Mar. 5, 2015.

(51) Int. Cl.
*A61B 5/00* (2006.01)
*A61B 5/1459* (2006.01)
(Continued)

(52) U.S. Cl.
CPC .......... *A61B 5/1459* (2013.01); *A61B 5/0022* (2013.01); *A61B 5/0071* (2013.01);
(Continued)

(58) Field of Classification Search
CPC ... A61B 5/0071; A61B 5/145; A61B 5/14503; A61B 5/14507; A61B 5/1451; A61B 5/14514; A61B 5/1459
See application file for complete search history.

(56) References Cited

U.S. PATENT DOCUMENTS 8,649,836 B2   2/2014  Shimizu et al.
9,302,903 B2 * 4/2016  Park ..................... A61B 5/1411
(Continued)

FOREIGN PATENT DOCUMENTS

WO    2014160804 A2    10/2014

OTHER PUBLICATIONS

Bandodkar et al., "Non-invasive wearable electrochemical sensors: a review," Trends in Biotechnology, vol. 32, No. 7, pp. 363-371, May 2014 (Abstract).
(Continued)

*Primary Examiner* — Max F Hindenburg
(74) *Attorney, Agent, or Firm* — Potomac Law Goup, PLLC; Mark Catan

(57) ABSTRACT

At least one microneedle comprises a hydrogel material that includes a substance that fluoresces when the substance interacts with an analyte. A magnitude of the fluorescence varies as a function of the concentration of the analyte. During use, the hydrogel material is illuminated with illumination light in a first wavelength range while the hydrogel
(Continued)

material interfaces with the dermal interstitial fluid layer of a subject, and a photosensor generates an output that corresponds to an amount of light received in a second wavelength range.

22 Claims, 9 Drawing Sheets

(51) Int. Cl.
| | |
|---|---|
| A61B 5/15 | (2006.01) |
| A61B 5/145 | (2006.01) |
| A61K 49/00 | (2006.01) |
| A61L 31/04 | (2006.01) |
| A61L 31/14 | (2006.01) |
| A61L 31/16 | (2006.01) |
| B29C 70/88 | (2006.01) |
| B29K 33/00 | (2006.01) |
| B29K 105/00 | (2006.01) |
| B29L 31/00 | (2006.01) |

(52) U.S. Cl.
CPC .......... *A61B 5/145* (2013.01); *A61B 5/14514* (2013.01); *A61B 5/14532* (2013.01); *A61B 5/14546* (2013.01); *A61B 5/150022* (2013.01); *A61B 5/150389* (2013.01); *A61B 5/150984* (2013.01); *A61B 5/685* (2013.01); *A61K 49/0017* (2013.01); *A61K 49/0073* (2013.01); *A61L 31/048* (2013.01); *A61L 31/145* (2013.01); *A61L 31/16* (2013.01); *B29C 70/88* (2013.01); *A61B 2560/0214* (2013.01); *A61B 2560/0242* (2013.01); *A61B 2562/12* (2013.01); *B29K 2033/26* (2013.01); *B29K 2105/0061* (2013.01); *B29K 2995/0035* (2013.01); *B29L 2031/7544* (2013.01)

(56) References Cited

U.S. PATENT DOCUMENTS

| | | | |
|---|---|---|---|
| 2009/0155918 A1* | 6/2009 | Payen | A61B 5/14539 436/149 |
| 2009/0182306 A1 | 7/2009 | Lee et al. | |
| 2009/0247984 A1 | 10/2009 | Lamego et al. | |
| 2009/0280064 A1* | 11/2009 | Papineni | A61B 5/0071 424/9.3 |
| 2010/0312483 A1 | 12/2010 | Peyser et al. | |
| 2011/0224515 A1 | 9/2011 | Mir et al. | |
| 2013/0324819 A1 | 12/2013 | Colvin | |
| 2013/0338039 A1 | 12/2013 | Mazed et al. | |
| 2013/0338632 A1* | 12/2013 | Kaplan | A61B 17/205 604/506 |
| 2014/0336487 A1* | 11/2014 | Wang | A61B 5/685 600/352 |
| 2015/0238433 A1* | 8/2015 | Yeung | A61K 9/0021 604/46 |
| 2016/0029937 A1 | 2/2016 | Sia et al. | |
| 2016/0089056 A1* | 3/2016 | Limaye | A61B 90/36 600/365 |
| 2016/0157764 A1* | 6/2016 | Di Palma | A61B 5/14865 600/347 |
| 2016/0158754 A1* | 6/2016 | Ziolkowski | C08F 2/48 422/502 |

OTHER PUBLICATIONS

International Search Report and Written Opinion for International Application No. PCT/US2016/020936 dated Jun. 9, 2016.
Jina et al., "Design, Development, and Evaluation of a Novel Microneedle Array-based Continuous Glucose Monitor," Journal of Diabetes Science and Technology, vol. 8, Issue 3, pp. 483-487, Mar. 6, 2014.
Roze et al., "Health-economic analysis of real-time, continuous glucose monitoring in people with Type 1 diabetes," Diabetic Medicine, vol. 32, No. 5, pp. 618-626, May 2015 (Abstract).
Vashist, "Non-invasive glucose monitoring technology in diabetes management: A review," Analytica Chimica Acta, vol. 750, pp. 16-27, Apr. 2012.
Vichai et al., Sulforhodamine B colorimetric assay for cytotoxicity screening,Nature Protocols (Aug. 17, 2006) vol. 1, No. 3; pp. 1112-1116.
Wang et al., "Minimally invasive extraction of dermal interstitial fluid for glucose monitoring using microneedles," Diabetes Technology and Therapeutics, vol. 7, Issue 1, pp. 131-141, Feb. 2005 (Abstract).
Caffarel-Salvador et al., "Hydrogel-forming microneedle arrays allow detection of drugs and glucose in vivo: potential for use in diagnosis and therapeutic drug monitoring," PloS One, Dec. 30, 2015, vol. 10(12), e0145644, pp. 1-21.
Miller et al., "Microneedle-based sensors for medical diagnosis," Journal of Materials Chemistry B., 2016 (full date is not available), vol. 4(8), pp. 1379-1383.

\* cited by examiner

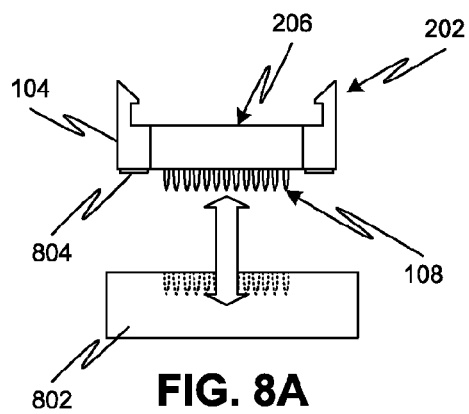 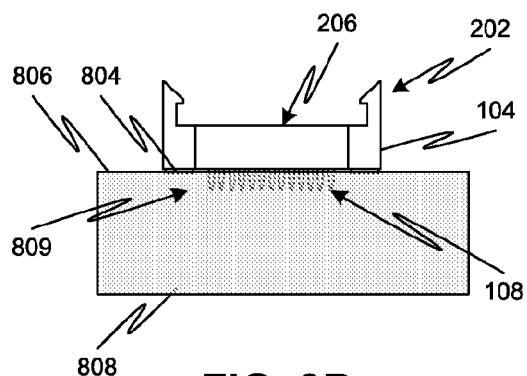
FIG. 8A　　　FIG. 8B
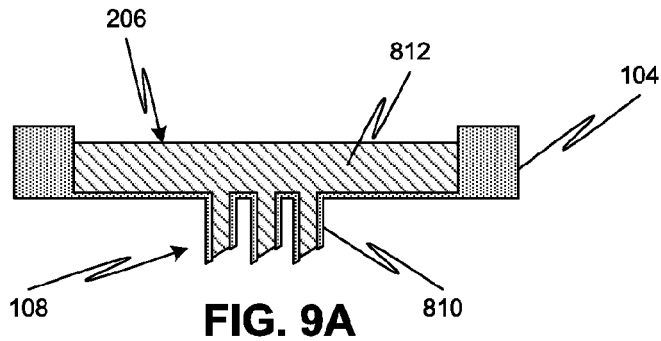
FIG. 9A
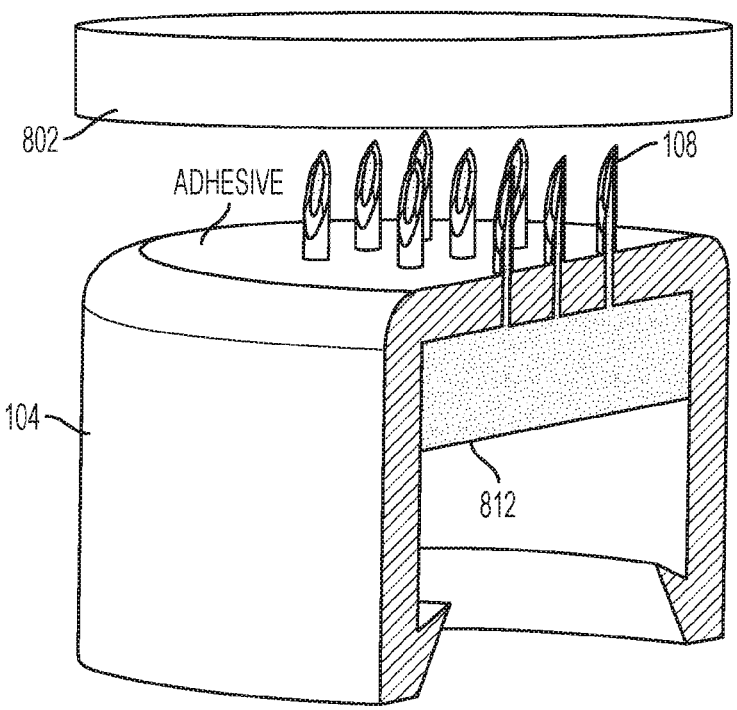
FIG. 9B

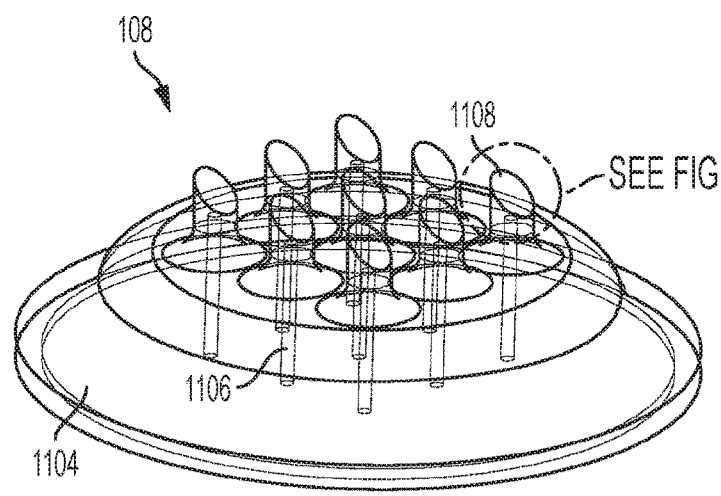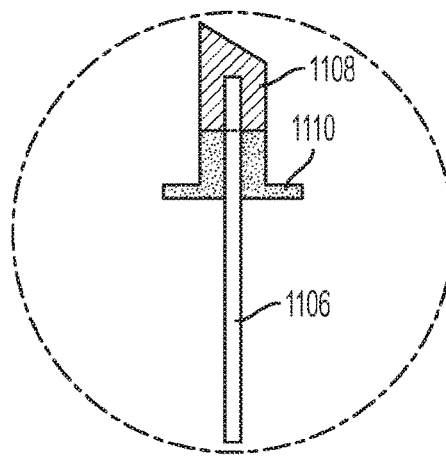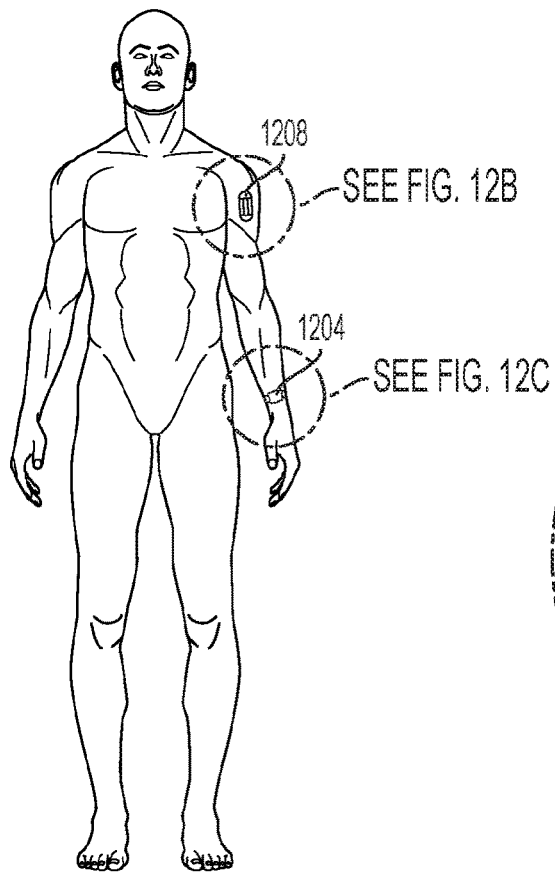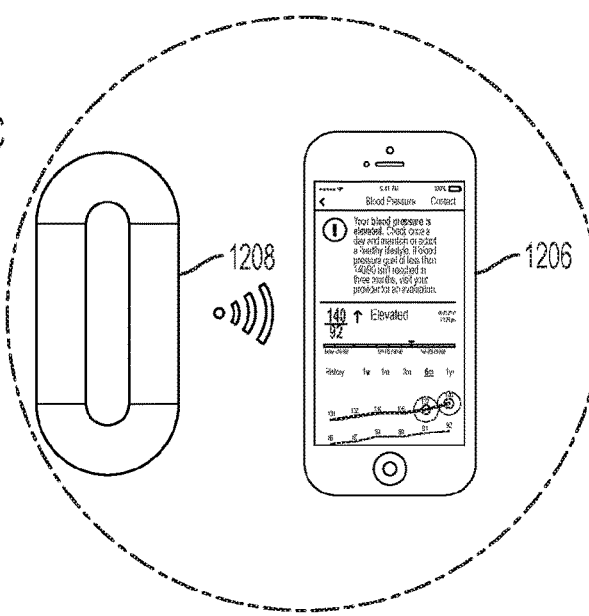
FIG. 11B
FIG. 11C
FIG. 12A
FIG. 12B

DEVICES AND SYSTEMS FOR OPTICALLY DETERMINING A CONCENTRATION OF AN ANALYTE IN A LIVING SUBJECT USING HYDROGEL-BASED, FLUORESCENT MICRONEEDLES AND METHODS OF MANUFACTURE THEREOF

CROSS REFERENCE TO RELATED APPLICATIONS

This Application is a National Stage Application under 35 U.S.C. § 371 of Application PCT/US2016/020936, filed Mar. 4, 2016, which claims the benefit of U.S. Provisional Application 62/128,973, filed Mar. 5, 2015. Each of the above-identified applications is incorporated herein by reference in its entirety.

BACKGROUND

The present disclosure relates generally to health tracking and diagnostic tools, and, more particularly, to systems, methods, and devices for continuous health parameter tracking and/or point-of-care diagnostics.

SUMMARY OF THE INVENTION

At least one microneedle comprises a hydrogel material that includes a substance that fluoresces when the substance interacts with an analyte. A magnitude of the fluorescence varies as a function of the concentration of the analyte. During use, the hydrogel material is illuminated with illumination light in a first wavelength range while the hydrogel material interfaces with the dermal interstitial fluid layer of a subject, and a photosensor generates an output that corresponds to an amount of light received in a second wavelength range.

BRIEF DESCRIPTION OF THE DRAWINGS

Embodiments will hereinafter be described with reference to the accompanying drawings, which have not necessarily been drawn to scale. Where applicable, some features may not be illustrated to assist in the illustration and description of underlying features. Throughout the figures, like reference numerals denote like elements.

FIG. 8A is a schematic diagram illustrating a sensing module, according to one or more embodiments of the disclosed subject matter.

FIG. 8B is a schematic diagram illustrating a sensing module applied to the skin, according to one or more embodiments of the disclosed subject matter.

FIG. 9A is a schematic diagram illustrating a cross-sectional view of a sensing module, according to one or more embodiments of the disclosed subject matter.

FIG. 9B is a three-dimensional model illustrating a sensing module, according to one or more embodiments of the disclosed subject matter.

FIG. 11B is a three-dimensional model of a sensing module and cross-sectional illustration of one microneedle of the sensing module, according to one or more embodiments of the disclosed subject matter.

FIG. 11C is a detail of a single microneedle from the FIG. 11B embodiment.

FIG. 12A illustrates use of the monitoring system for health parameter tracking and/or point-of-care diagnostic measurement, according to one or more embodiments of the disclosed subject matter.

FIG. 12B is a detail of a patch-mounted embodiment for health parameter tracking and/or point-of-care diagnostic measurement, according to one or more embodiments of the disclosed subject matter.

DESCRIPTION OF THE PREFERRED EMBODIMENTS

In embodiments of the disclosed subject matter, a wearable monitoring system can be used to track health parameters of a patient and/or to provide point-of-care diagnostics. The monitoring system can include a sensing module that passively conveys information regarding the health parameter or condition, for example, by employing a substance (e.g., a polymer) in contact with a biological fluid from a patient and that changes properties (e.g., fluorescence) based on the health parameter or condition.

Some embodiments rely on a substance that fluoresces in a second wavelength range when illuminated by light in a first wavelength range when the substance interacts with an analyte. For example, when the analyte is glucose, the sensing module can employ a glucose-responsive polymer for which a magnitude of the fluorescence varies as a function of the concentration of the analyte. The monitoring system can also include an interrogation module that is coupled to the sensing module. For example, the interrogation module may include an interrogating light source that generates light at the first wavelength and associated optics for interrogating the polymer of the sensing module. The interrogation module can further include a photodetector and associated optics for processing a fluorescent signal at the second wavelength generated by the polymer as a result of exposure to the interrogating light in the presence of the analyte. In some embodiments, the sensing module may be a disposable or consumable component while the interrogation module may be a separate reusable or recyclable component. Additional components can be provided to process and/or store data from the interrogation module and/or to communicate with external systems, such as, but not limited to, smartphone and tablets, remote computer terminals or servers, computer networks, and the Internet.

Figure 1:
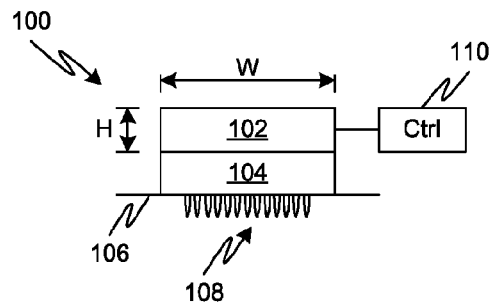
FIG. 1 is a schematic diagram illustrating components of a monitoring system, according to one or more embodiments of the disclosed subject matter.
Figure 2:
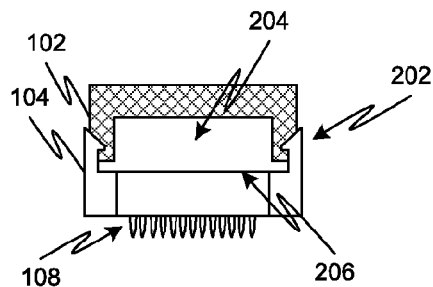
FIG. 2 is a simplified schematic diagram illustrating a cross-sectional view of an interrogation module and a sensing module of a monitoring system, according to one or more embodiments of the disclosed subject matter.

FIGS. 1-2 illustrate components of a monitoring system 100, which can include a sensing module 104 and an interrogation module 102. The sensing module 104 can include a patient interfacing component, e.g., a microneedle array 108, that interfaces with a biological fluid of the patient. For example, the microneedle array 108 can penetrate the stratum corneum of the skin 106 so as to access the dermal interstitial fluid layer and interface with that layer and to detect parameters of the fluid therein, e.g., glucose concentration, electrolytes, hormones, lactate, urea, amino acids, proteins, enzymes, co-enzymes, triglycerides, cholesterol, or any other useful parameter.

The interrogation module 102 can be releasably coupled to the sensing module 104, for example, by a snap-fit coupling 202. Coupling of the interrogation module 102 and the sensing module 104 can occur, for example, prior to or after attachment of the sensing module 104 to the skin 106 of a patient. The interrogation module 102 can have a width, W, (e.g., a diameter or maximum cross-sectional dimension) of approximately 20 mm or less and a height, H, (i.e., in a direction perpendicular to the skin surface 106) of approximately 10-25 mm or less. Coupling of the interrogation module 102 to the sensing module 104 can create a light-tight internal volume 204 whereby appropriate optical components (not shown in FIG. 2) can direct excitation light at an interrogating surface 206 (e.g., a surface of a fluorescent polymer or an input to a waveguide interfacing with a fluorescent polymer). The interrogation module 102 can communicate with an external control unit 110 or other system, network, or module, via a wired or wireless connection.

In one or more embodiments, the interrogation module comprises a miniaturized fluorescent light signal detector, which allows for use in continuous tracking of health parameters as a wearable device, and in point-of-care diagnostic devices. The miniaturized light signal detector can provide excitation light energy to a fluorescent compound of interest, for example, a fluorescence sensor with chemical sensor conjugated to a fluorophore contained in the sensing module. The fluorophore emits light in a second wavelength range in response to exposure to light in a first wavelength range in the presence of the analyte of interest. Since the magnitude of the fluorescence varies as a function of the concentration of the analyte, the interrogation module can detect and quantify the fluorescent light emitted from the compound of interest, and process the fluorescent light signal in order to translate it to a clinically relevant value, e.g. relative glucose concentration level.

Figure 3A:
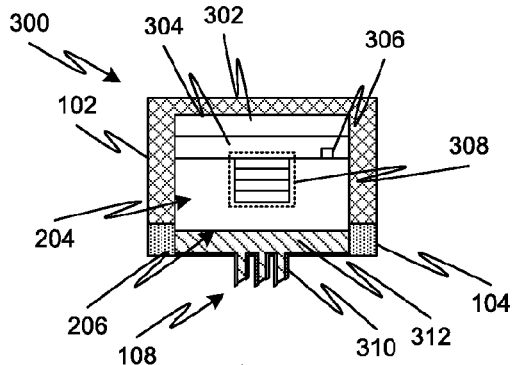
FIG. 3A is a schematic diagram illustrating a cross-sectional view of an interrogation module employing an illumination/detection stack, according to one or more embodiments of the disclosed subject matter.
Figure 3B:
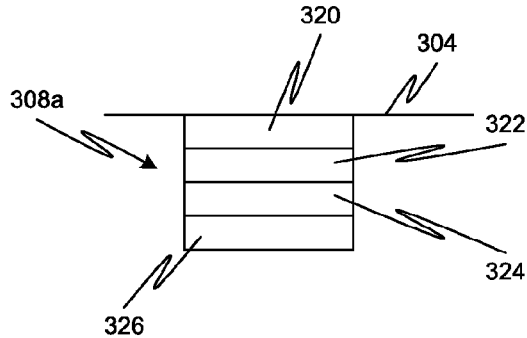
FIG. 3B is a schematic diagram illustrating a close-up view of the illumination/detection stack of FIG. 3A, according to one or more embodiments of the disclosed subject matter.

For example, the miniaturized light signal detector 308 can include a stack arrangement of light source 326, detector 320, and corresponding optics, as illustrated in FIGS. 3A-3B. In particular, the monitoring system 300 includes an interrogation module 102 with an insulated housing coupled to the sensing module 104 with microneedle array 108. The detection system 308 of the interrogation module 102 is constructed as a stack such that the illumination and detection are provided directly adjacent to the interrogating surface 206 of the substance/compound 312 emitting fluorescent light. The stack 308 includes, in order, a light source 326 (e.g., a light-emitting diode (LED)), an angle-of-incidence (AOI) filter 324, a wavelength selective filter 322 (e.g., an ultra-violet (UV) light filter), and a photosensor 320 (e.g., a photodiode). The photosensor 320 detects light in the second wavelength range that was emitted by the fluorophore. The wavelength selective filter 322 attenuates light in the first wavelength range and transmits light in the second wavelength range.

In some embodiments, the light source 326 may be similar in size to the photosensor 320, e.g., as shown in the configuration 308a of FIG. 3B, in which case the light source 326 may be substantially (at least 70%) transparent to the fluorescent light to be detected by the photosensor 320. Alternatively or additionally, the light source may be substantially smaller (e.g., no more than 50% of the width) of the photosensor 320, for example, as shown by light sensor 336 in the configuration 308b of FIG. 3C.

Figure 3C:
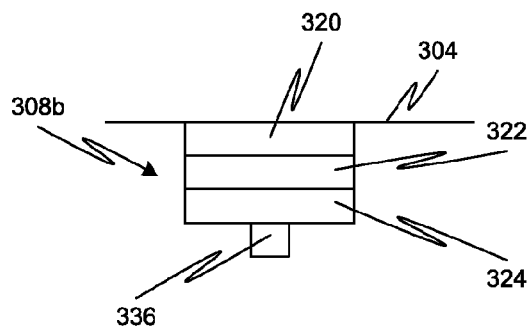
FIG. 3C is a schematic diagram illustrating a close-up view of the illumination/detection stack employing a light source smaller than the photodetector, according to one or more embodiments of the disclosed subject matter.
Figure 3D:
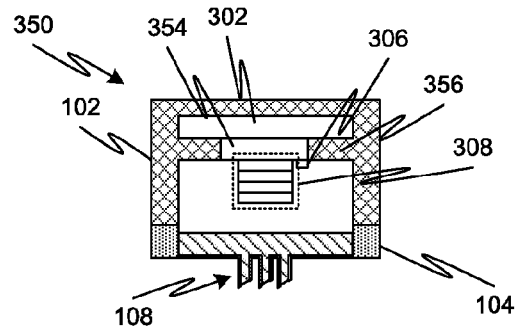
FIG. 3D is a schematic diagram illustrating a cross-sectional view of a first variation for an interrogation module, according to one or more embodiments of the disclosed subject matter.
Figure 3E:
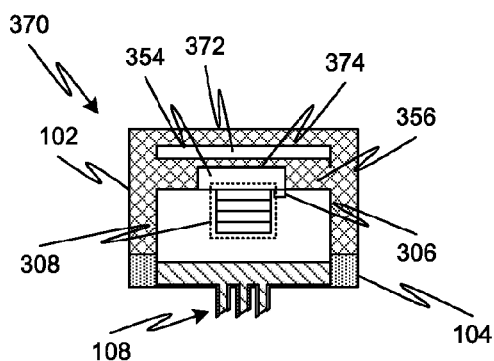
FIG. 3E is a schematic diagram illustrating a cross-sectional view of a second variation for an interrogation module, according to one or more embodiments of the disclosed subject matter.
Figure 3F:
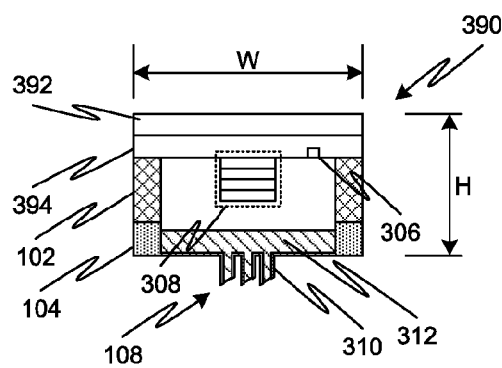
FIG. 3F is a schematic diagram illustrating a cross-sectional view of a third variation for an interrogation module, according to one or more embodiments of the disclosed subject matter.
Figure 3G:
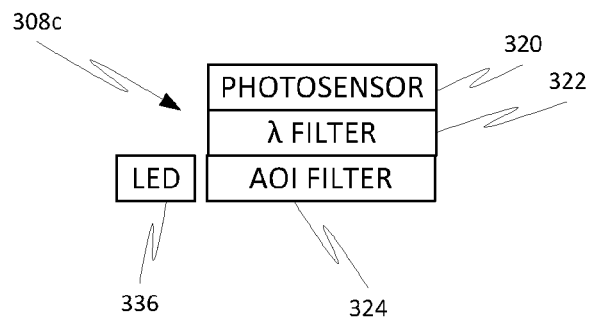
FIG. 3G is a schematic diagram illustrating an illumination/detection stack in which the light source is offset laterally to the side of the photodetector and filter, according to one or more embodiments of the disclosed subject matter.
Figure 3H:
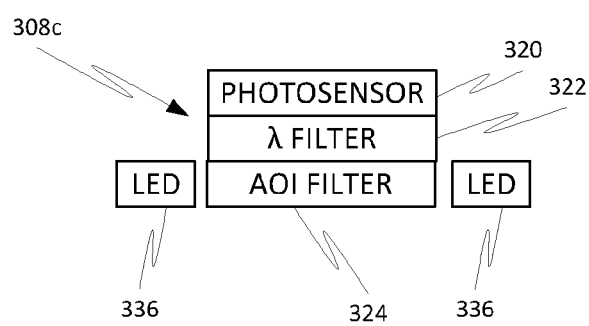
FIG. 3H is a schematic diagram illustrating an illumination/detection stack in which a plurality of light sources are offset laterally to the side of the photodetector and filter, according to one or more embodiments of the disclosed subject matter.

In other embodiments, the light source 326 may be positioned laterally off to the side of the stack 308c, as shown in FIG. 3G. In this case, the stack 308c includes, in order, an AOI filter 324, a wavelength selective filter 322 and a photosensor 320. A single light source 326 may be used as shown in FIG. 3G. Alternatively, a plurality of light sources 326 may be positioned laterally off to the side of the stack 308c, as shown in FIG. 3H. In these embodiments, the light sources illuminate the microneedles, which are located below the stack 308c.

The interrogating module 102 can further include a processor, such as a printed circuit board 304 (PCB), and a power source 302, such as a battery. A temperature sensor 306 can be provided proximal to the stack 308 for monitoring a temperature within the monitoring system 300 and for adjusting results obtained by the photosensor 320 responsively thereto. Since temperature variations can skew obtained results, the housing of the interrogation module 102 (and/or the sensing module 104) may be provided with insulation throughout to maintain the temperature of the monitoring system 300 substantially constant. Alternatively or additionally, active temperature control components, such as thermoelectric cooler (TEC), may also be provided.

Figure 4:
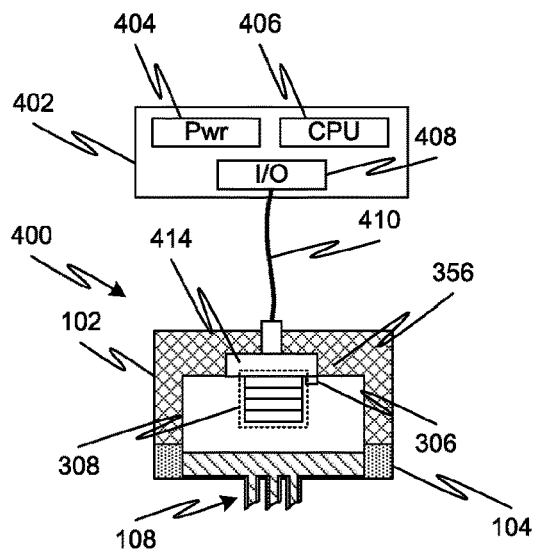
FIG. 4 is a schematic diagram illustrating an interrogation module employing an illumination/detection stack and remote power and processing module, according to one or more embodiments of the disclosed subject matter.

In some embodiments, the size of the PCB may be reduced and provided with additional insulation, for example, as illustrated by PCB 354 and extra insulating portions 356 in system 350 of FIG. 3D. Alternatively or additionally, the PCB may be thermally isolated from the battery by additional insulating portions, for example, as illustrated by the spacing of battery 372 from PCB 354 by insulating portion 374 in system 370 of FIG. 3E. In yet another alternative, the PCB 394 and/or battery 392 may extend all or at least most of the width (W) of the interrogating module 102 with or without additional insulating portions, as illustrated in system 390 of FIG. 3F. In still another alternative illustrated in system 400 of FIG. 4, the interrogating module 102 can include a mounting board 414 that supports the stack 308 and communicates data from the stack 308 to the input/output connection 408 of a remote unit 402 via line 410. The remote unit 402 may provide power (e.g., via a battery 404 or other power supply) and processing (e.g., via central processing unit 406 or other processor) for the interrogating module 102 without unnecessarily subjecting the interrogating module 102 to possible thermal variations or loads.

Returning to FIG. 3B, the light source 326 of the stack 308 can be an LED. The LED 326 can have a central wavelength in the first wavelength range that corresponds to the maximum excitation peak of the fluorophore compound in the sensing module 104 (e.g., material 310 and/or 312). For fluorescent light to be able to reach the detector 320 located behind/above the LED 326, the LED 336 can either be significantly smaller that the detector 320 (as shown in FIG. 3C) or transparent to light of wavelengths greater than the central emitted wavelength. The LED 326 can be fixed onto the AOI filter 324 using optical epoxy or any other compatible fixation system or compound.

The AOI filter 324 can prevent light of high angles of incidence from reaching the photosensor 320, by acting as a pre-filter for the wavelength selective filter 322, which may otherwise have reduced filtering efficiency for light having a high incidence angle. For application in filtering the high incidence angle light signal, a low numerical aperture can be used. For example, the AOI filter 324 can comprise one or more of a fiber optic plate, a fiber optic faceplate, and a bundle or array of coherent optical fibers. The AOI filter 324 can be fixed to the wavelength selective filter 322 using optical epoxy or any other compatible fixation system or compound. Note that the use of an AOI filter is not mandatory, and the AOI filter may be omitted in any of the embodiments described herein. When the AOI filter is omitted, the photosensor 320, the wavelength selective filter 322, and the LED 326 can be integrated onto a single silicon chip. This can help reduce the thickness of the device.

The wavelength selective filter 322 prevents excitation light from reaching the photosensor 320 and saturating it. For example, if UV excitation light is used and the wavelength selective filter 322 is a UV filter, the filter would attenuate light in the UV wavelength range. The wavelength selective filter can be fixed to the glass input of the photosensor 320 using optical epoxy or any other compatible fixation system or compound. Alternatively or additionally, the wavelength selective filter 322 can be formed by coating the filter material, which may be an absorbing material or a stack of several different materials to create destructive interference, onto the input window of the photosensor 320 or onto the back surface (i.e., the surface between the AOI filter 324 and the photosensor 320) of the AOI filter 324. Alternatively or additionally, the glass input window of an existing photosensor 320 can be replaced with an appropriate wavelength selective filter. Appropriate absorbing materials include, but are not limited to, silicon (Si), polysilicon (poly-Si), and silicon carbide (SiC). Other materials with an appropriate transition between the desired absorption and transmission wavelengths are also possible according to one or more contemplated embodiments.

The photosensor 320 can include one or more photodiodes that detect fluorescent emission in the second wavelength range from the sensing module 104. For example, multiple photodiodes can be used to monitor the excitation power for differential measurement. However, a single photodiode is sufficient for standard detection of fluorescent light. Alternatively or additionally, the photosensor 320 can be a charge-coupled device (CCD) camera. In such a configuration, the signal from different fluorescent light sources, with unique emission wavelengths, can be individually addressable. In this situation, a plurality of wavelength selective filters with different wavelength cutoffs would be used for respective different regions of the CCD.

The PCB 304 can host electronics that, among other things, control the excitation light source from the LED 326, process the detected fluorescent light signal from the photosensor 320 (e.g., by using a microcontroller), amplify the detected fluorescent light signal, provide offset removal, calibrate the system at both the factory and user level, provide temperature correction, and allow for communication with separate systems (e g., using wireless protocol, such as Bluetooth, and/or to communicate with a smartphone, smart watch, or other remote system).

A temperature sensor 306 can take temperature measurements to allow the PCB 304 to account for temperature dependency of the photosensor 320 and/or the fluorophore in the sensing module 104. Many different types of temperature sensors 306 can be employed in the monitoring system according to one or more contemplated embodiments. For example, a platinum (Pt) resistor, which can be printed using printed electronics, can be used to provide temperature measurements, in either a four-point measurement configuration or as a voltage divider and voltage follower setup. Other commercially available temperature sensors are also possible, such as thermocouples, thermistors, resistance temperature detectors (RTDs), and infrared thermography. Although only one temperature sensor 306 has been illustrated in the figures, it is also possible to use multiple temperature sensors, for example, to measure changes in temperature of the system (due to external environmental change or heating from the detector device) and/or changes in skin surface temperature.

Figure 5A:
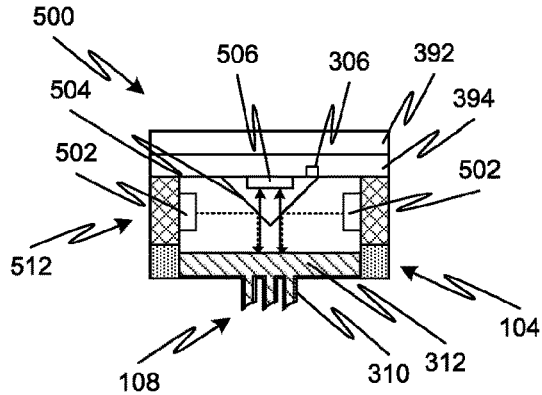
FIG. 5A is a schematic diagram illustrating a cross-sectional view of an interrogation module employing a four-panel beam splitter, according to one or more embodiments of the disclosed subject matter.
Figure 5B:
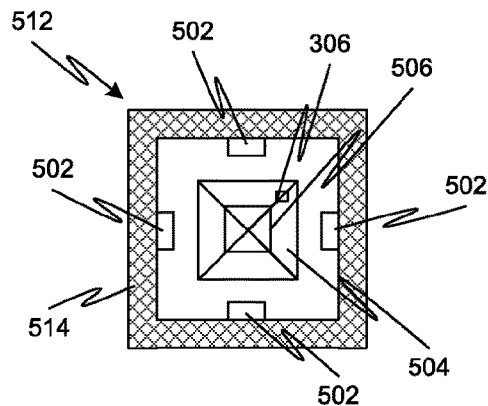
FIG. 5B is a bottom view of an interrogation module of FIG. 5A.

In another example, the miniaturized light signal detector can be achieved using a spaced arrangement between the light source 502 and the detector 506, as illustrated in FIGS. 5A-5B. In particular, the monitoring system 500 includes an interrogation module 512 with an insulating housing coupled to the sensing module 104 with microneedle array 108. The detection system of the interrogation module 512 is constructed such that four light sources (e.g., LEDs 502) are equally spaced along the circumference of the module 512. In place of the AOI and wavelength selective filters of FIGS. 3A-3H, or in addition to such AOI and wavelength selective filters, the interrogation module 512 can include a beam splitter 504 to direct excitation and fluorescent light along appropriate paths. Thus, the LEDs 502 can direct their excitation light (dotted arrow line) laterally at a centrally located beam splitter 504 (e.g., a dichroic or dielectric beam splitter) that reflects the excitation light at the fluorescing polymer 312 interfacing with the needles 310. The resulting fluorescence (solid arrow line) emitted by the polymer 312 passes through the beam splitter 504 to be incident on the photosensor 506. The configuration of the battery 392 and PCB 394 on which the photosensor 506 is mounted can be varied similar to the embodiments described above with respect to FIGS. 3A-3H and FIG. 4.

Figure 5C:
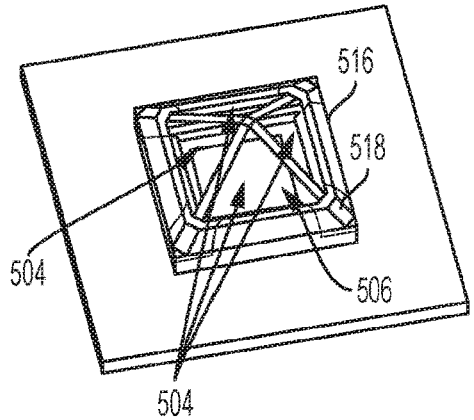
FIG. 5C is a three-dimensional model illustrating a beam splitter for use in the interrogation module of FIG. 5A.
Figure 5D:
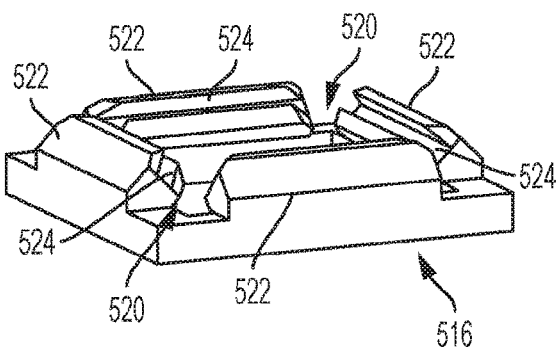
FIG. 5D is a three-dimensional model illustrating a base holder for plates of the beam splitter of FIG. 5C.
Figure 5E:
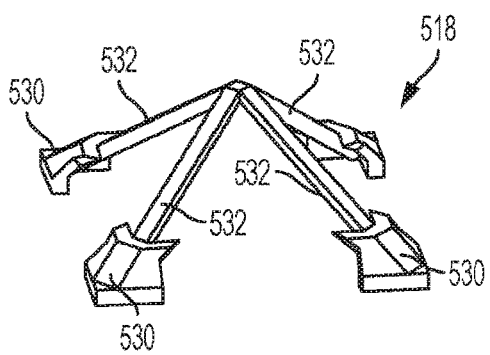
FIG. 5E is a three-dimensional model illustrating a cap for plates of the beam splitter of FIG. 5C.

The beam splitter can have four separate triangular plates 504 that are positioned in the shape a pyramid, as illustrated in FIG. 5C. The plates 504 of the beam splitter can be held in place and at the appropriate angle for illumination of the fluorophore of the sensing module 104 by a base holder 516 and a cap 518. The base holder 516 can have four arms 522, each with a respective slot 524 for holding a first edge of the plate 504 therein. The base holder 516 can be attached to the PCB 394, for example by epoxy, glue, screws, or any other fixation method, with the photosensor 506 at a middle or center of the base holder 516. The base holder 516 can further include a gap 520 between adjacent arms 522, into which the anchor points 530 of cap 518 fit. The arms 532 of the cap 518 further support the beam splitter plate 504 along the second and third edges thereof. The cap 518 can be attached to the plates 504 and/or the base holder 516 using epoxy, glue, or any other fixation method.

Figure 6A:
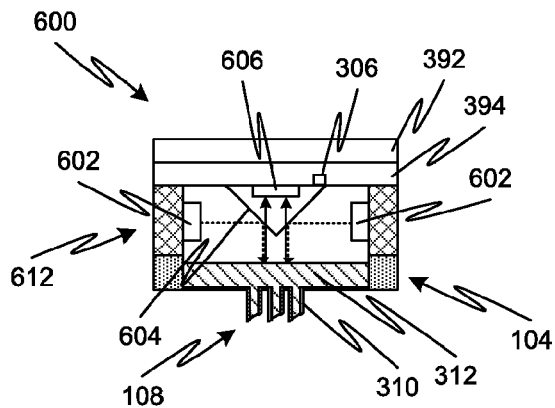
FIG. 6A is a schematic diagram illustrating a cross-sectional view of an interrogation module employing a two-panel beam splitter, according to one or more embodiments of the disclosed subject matter.
Figure 6B:
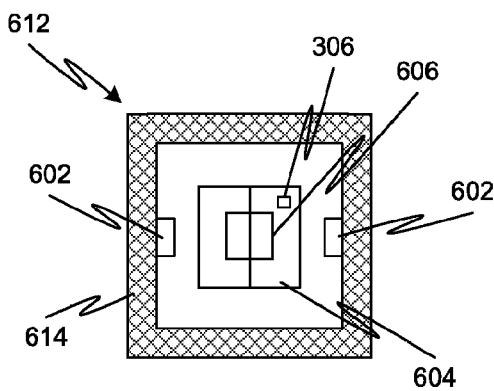
FIG. 6B is a bottom view of an interrogation module of FIG. 6A.
Figure 7A:
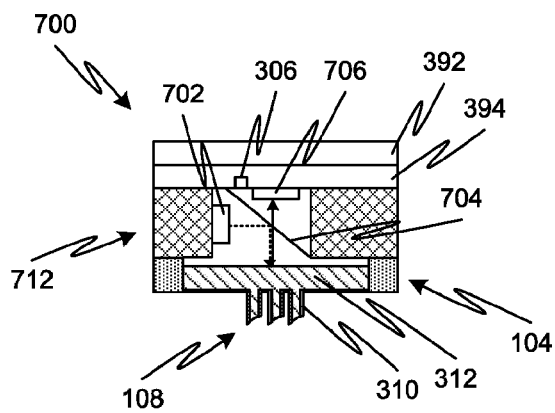
FIG. 7A is a schematic diagram illustrating a cross-sectional view of an interrogation module employing a single panel beam splitter, according to one or more embodiments of the disclosed subject matter.
Figure 7B:
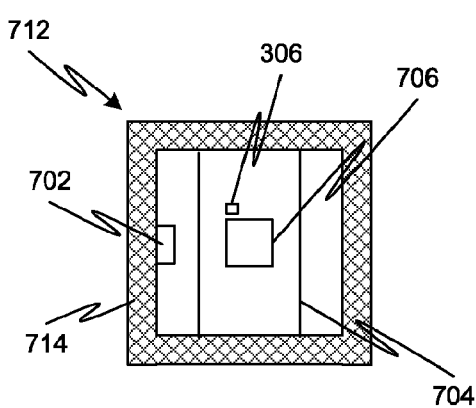
FIG. 7B is a bottom view of an interrogation module of FIG. 7A.

In some embodiments, the number of LEDs 502 and beam splitter plates 504 can be less than the four illustrated in FIGS. 5A-5B. For example, the interrogation module 612 may have two LEDs 602 and two beam splitter plates 604 in a 180° orientation, thereby forming a triangular prism polyhedron shape, as illustrated by monitoring system 600 of FIGS. 6A-6B. In another example, the interrogation module 712 may have a single LED 702 and a single beam splitter plate 704, as illustrated by monitoring system 700 of FIGS. 7A-7B. Other numbers of LEDs and different configurations/numbers of beam splitter plates are also possible according to one or more contemplated embodiments.

Figure 6C:
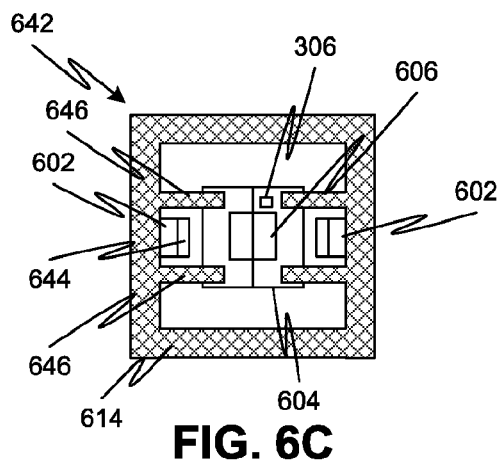
FIG. 6C is a schematic diagram illustrating a bottom view of a first variation for an interrogation module employing a two-panel beam splitter, according to one or more embodiments of the disclosed subject matter.
Figure 6D:
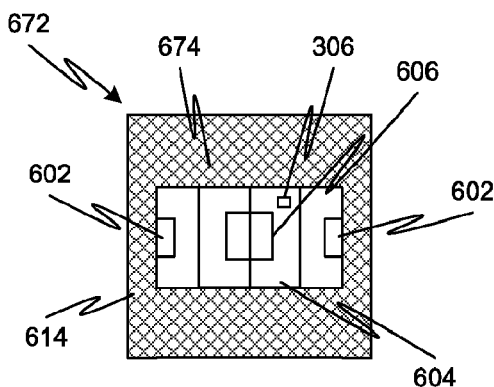
FIG. 6D is a schematic diagram illustrating a bottom view of a second variation for an interrogation module employing a two-panel beam splitter, according to one or more embodiments of the disclosed subject matter.

In some embodiments, additional insulating portions and/or waveguiding elements and/or light-blocking elements may be provided in the interior of the interrogation module to prevent stray light from inadvertently reaching the photosensor and/or fluorophore regions beyond those intended to interrogation. For example, the housing 614 of the interrogation module 642 can include projections 646 to prevent light from spreading beyond a desired beam waist, as illustrated in FIG. 6C. Alternatively or additionally, collimating optics 644 can be provided in the beam path between the LED 602 and the beam splitter 604 and/or in the beam path the fluorophore and the beam splitter 604 (not shown) and/or in the beam path between the beam splitter 604 and the photosensor 606. Alternatively or additionally, the housing 614 of the interrogation module 672 can be extended to have thicker walls along the beam path, which may be coated with a non-reflective coating to minimize reflections, thereby reducing an interior volume of the interrogation module 672, as illustrated in FIG. 6D.

Figure 12C:
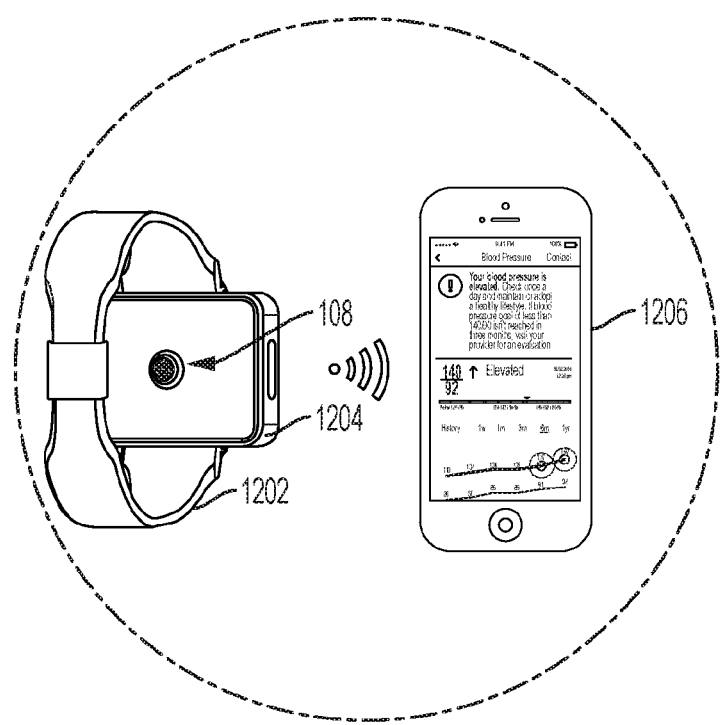
FIG. 12C is a detail of a wristband-mounted embodiment for health parameter tracking and/or point-of-care diagnostic measurement, according to one or more embodiments of the disclosed subject matter.

In one or more embodiments, the monitoring system can be used as a standalone device 1208 or coupled to a smart watch 1204, as illustrated, for example, in FIGS. 12A-12C. When coupled to a smart watch 1204, the monitoring system may not be required to have its own battery and wireless connectivity system (e.g., to a separate smart phone 1206 or other device). Instead, the functions served by these elements can be provided by the smart watch 1204.

In one or more embodiments, the monitoring system may be used as a wearable, minimally-invasive system for continuously monitoring one or more parameters of the wearer, such as, but not limited to detecting glucose, electrolytes, hormones, lactate, urea, amino acids, proteins, enzymes, co-enzymes, cholesterol, and triglycerides. For example, the monitoring system can be used to monitor glucose concentration within the wearer by using a glucose-responsive polymer in the sensing module.

For example, the sensing module 104 includes one or more microneedles (shown as array 108 in FIG. 8A, although a single microneedle is also possible). For example, the microneedles can have a height of 1000 µm (in a direction parallel to an axis thereof). The microneedles may be hollow, for example, having an inner diameter of between 100 µm and 200 µm and a wall thickness of 20 µm. The size of the microneedles allows the sensing module 104 to access the dermal interstitial fluid 809 of the skin 806 of the wearer in a minimally invasive manner, i.e., the limited height of the microneedle in insufficient to reach the capillary bed 808, which would cause bleeding, but is sufficient to penetrate the stratum corneum of the skin to access dermal interstitial fluid 809. The microneedle can include a glucose responsive polymer as the sensing material, thereby allowing the sensor to dwell within the dermal interstitial fluid for continuous monitoring. Each of the microneedles can further include a bevel to reduce pain during insertion. The sensing module 104 can be held to the skin by an adhesive 804, which may surround the array 108 such that when adhered to the skin a light-tight seal is formed around the array 108 to prevent inadvertent excitation of the fluorophore in the microneedles.

In some embodiments, the microneedle array 108 is formed as a hollow scaffold 810 and filled with a glucose-responsive hydrogel 812, as illustrated in FIGS. 9A-9B. For example, the hollow scaffold can be formed of a biocompatible material such as, but not limited to, polyether ether ketone (PEEK) or medical-grade stainless steel (316/316L).

The glucose-responsive hydrogel can be formed by glucose-responsive dye conjugated to poly(2-hydroxyethyl methacrylate) or polyacrylamide. For example, the dye can be dibronic acid and pyrene dye having an excitation wavelength at 342 nm and an emission wavelength at 397 nm and 417 nm, respectively. The resulting fluorescence signal can be correlated to pre-calibrated glucose concentrations and can provide specificity within 60-200 mg/dL. In this and other embodiments, a protective padding 802 can be provided over the needle array 108 to protect the needles, keep the hydrogel from drying out, and/or cover the adhesive 804 prior to use by the wearer.

Figure 10A:
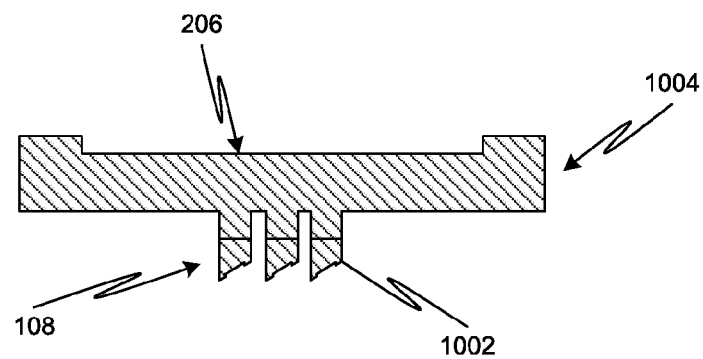
FIG. 10A is a schematic diagram illustrating a cross-sectional view of a first variation of a sensing module, according to one or more embodiments of the disclosed subject matter.
Figure 10B:
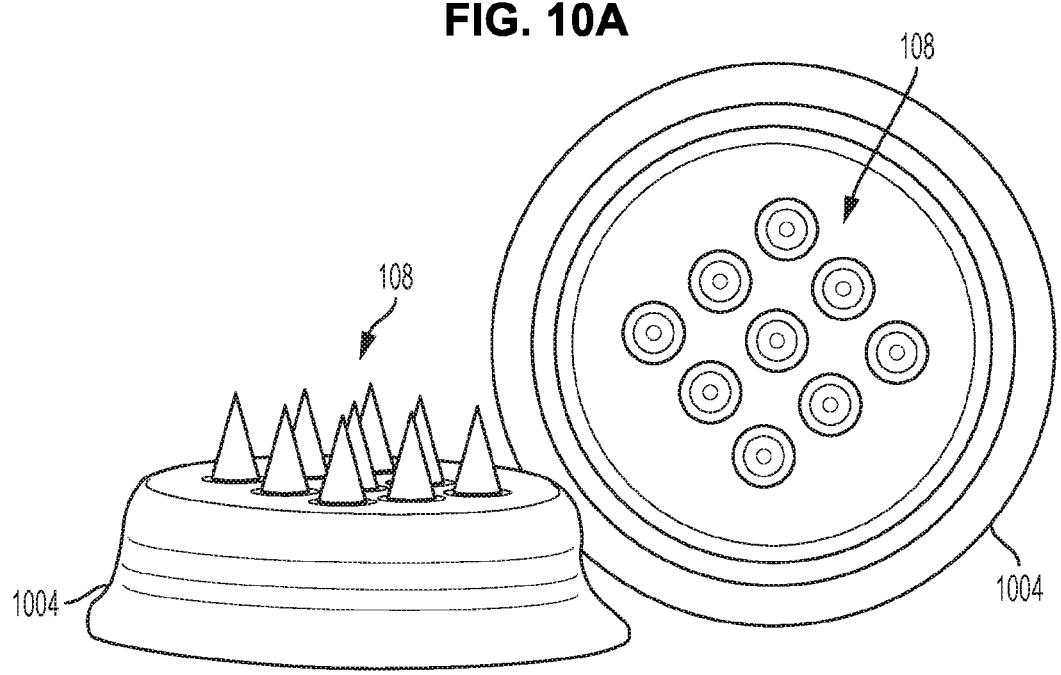
FIG. 10B is an image showing side and bottom views of a sensing module, according to one or more embodiments of the disclosed subject matter.

In some embodiments, the microneedle array can be formed without a hollow scaffold. In such a configuration, the microneedle array 108 of the sensing module 1004 may be formed wholly or partially of the glucose-responsive hydrogel, as illustrated in FIGS. 10A-10B. In these embodiments, the hydrogel is not enclosed in a metal or other solid structure. For example, the microneedles can be wholly fabricated of hydrogel, poly(2-hydroxyethyl methacrylate) or polyacrylamide. These microneedles can be used in the "dry" state, since they exhibit increased mechanical strength when the hydrogel is dehydrated. The glucose-responsive hydrogel may be localized at the tip 1002 of the microneedles (e.g., the top 200 μm) or the entire microneedle shaft (not shown). When the tip 1002 of the microneedle is formed of glucose-responsive hydrogel, the rest of the body can also be formed of the same hydrogel but without glucose-responsive dye conjugated to the matrix.

To reduce deformation of the microneedles when the hydrogel dries, the microneedles may be formed by drying a hydrated hydrogel material having a shrinkage percentage of less than 30%. When polyacrylamide hydrogel is used, a polyacrylamide hydrogel having a high percentage of AAm and a low AAm/MBAm ratio may be used. For example, polyacrylamide hydrogel with an AAm percentage between 28 and 32 and an AAm/MBAm ratio between 14 and 16 may be used, or polyacrylamide hydrogel with an AAm percentage between 29 and 31 and an AAm/MBAm ratio between 14.5 and 15.5 may be used. In some preferred embodiments, a polyacrylamide hydrogel with an AAm percentage of 30 and an AAm/MBAm ratio of 15 is used. These ranges of parameters yield dried hydrogel microneedles that provide improved penetration of the stratum corneum of the skin and access to the dermal interstitial fluid. They also transmit light in the first wavelength range and the second wavelength range. Immersing the hydrogel in a bath of ethanol (e.g., for one hour) prior to drying also improves the performance of the hydrogel microneedles by stabilizing the surface of the hydrogel microneedles.

Figure 10C:
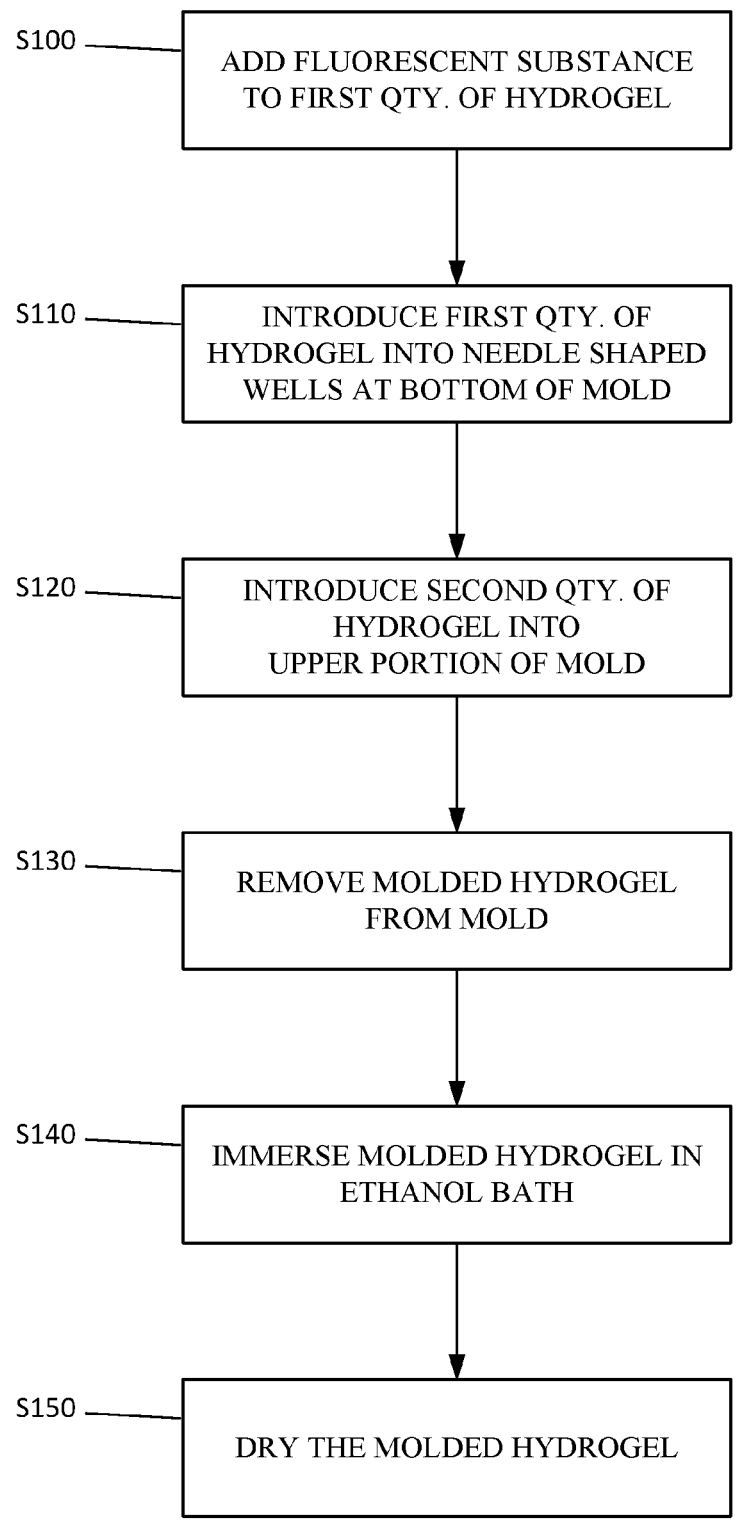
FIG. 10C is a flowchart of a process for forming an array of hydrogel microneedles affixed to a base.

In some embodiments, an array of hydrogel microneedles affixed to a base may be fabricated using the process depicted in FIG. 10C. In step S100, the fluorescent substance is added to a first quantity of hydrogel material. In step S110, the first quantity of hydrogel material with the added fluorescent substance is introduced into a plurality of needle shaped wells located at a bottom of a mold. The mold may have a negative space that corresponds to the positive space of the end product depicted in FIG. 10B. In step S120, a second quantity of hydrogel material is then introduced into an upper portion of the mold above the first quantity of hydrogel material disposed in the needle shaped wells. The second quantity of hydrogel material will eventually serve as a base for the first quantity of hydrogel material disposed in the needle shaped wells. After formation, the molded hydrogel is removed from the mold in step S130. Optionally, it is immersed in an ethanol bath (e.g., for one hour) in step S140. It is then dried in step S150. The result is a hydrogel material that transmits light in the first wavelength range and transmits light in the second wavelength range. Optionally, the top of the second quantity of hydrogel material (i.e., the side that is opposite from the microneedles) is shaped to have a concave shape. This shape can help focus the light onto the photosensor.

In some embodiments, the fluorescent substance is not incorporated into the second quantity of hydrogel material. In some embodiments, there are at least four needle shaped wells. In some embodiments, there is a two dimensional array of needle shaped wells. In some embodiments, this array is a 3×3 array of needle shaped wells. In some embodiments, the needle shaped wells have diameters between 175 and 225 μm and lengths between 1300 and 1500 μm.

Figure 11A:
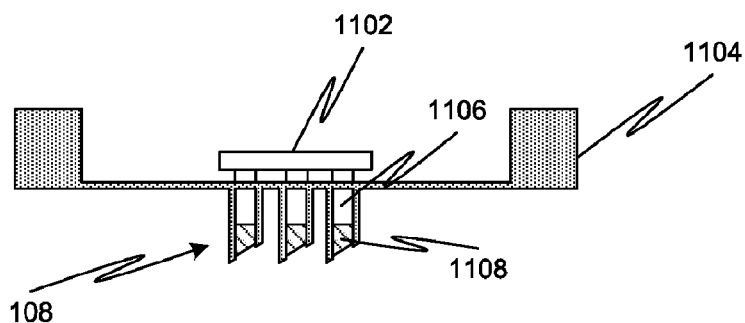
FIG. 11A is a schematic diagram illustrating a cross-sectional view of a second variation of a sensing module, according to one or more embodiments of the disclosed subject matter.

In some embodiments, the microneedle array can be formed with an optical fiber to convey fluorescent light from the tip to the detection surface of the sensing module 1104. For example, the core of each microneedle can include a multimode optical fiber 1106, as illustrated in FIG. 11A. Light to/from the glucose-responsive polymer tip 1108 can be conveyed by the optical fiber 1106. One or more optical components 1102, such as lenses and/or filters, can be provided to couple light into and out of the individual optical fibers 1106.

In some embodiments, the sensing module 1104 can have a microneedle array 108 where each microneedle has a glucose-responsive hydrogel tip 1108, a hydrogel body 1110, and a multimode optical fiber core 1106, as illustrated in FIGS. 11B and 11C. The optical fiber core 1106 can provide more mechanical strength to help the dehydrated hydrogel 1108 penetrate through the stratum corneum of the skin, as well as convey light from the excitation source to the microneedles and from the microneedles back to the photosensor. The tips of microneedles to the back of the array can be transparent to enable light transmittance between the detector system and the microneedle tip.

In any of the disclosed embodiments, one or more of the microneedles can have a height in a range of 500-2000 μm, an outer diameter in a range of 40-200 μm, a bore diameter in a range of 100-200 μm for PEEK and greater than or equal to 200 μm for stainless steel, an aspect ratio of height to diameter of less than or equal to 25:1, and an array diameter or maximum cross-width dimension less than 1 cm. However, the above noted dimensions and features are meant to be exemplary only, and other dimensions and features are also possible according to one or more contemplated embodiments.

The sensing module, in particular the microneedle or microneedles thereof, interact with glucose in the dermal interstitial fluid and produce a signal in the form of fluorescent light intensity to indicate the glucose concentration in the dermal interstitial fluid. The higher the glucose concentration, the higher the fluorescent light intensity will be. As noted above, the fluorescent signal can be achieved using a glucose-responsive dye conjugated to the hydrogel matrix (poly(2-hydroxyethyl methacrylate) or polyacrylamide). The glucose-responsive dye molecule has a saccharide binding site, a dye to emit fluorescent light with intensity corresponding to glucose concentration, a monomer site to allow for the entire molecule to the polymer matrix. This method of dye incorporation prevents the dye from leaching out of the polymer matrix into the skin.

In any of the disclosed embodiments, the sensing module, in particular the microneedle array, can be applied to the skin surface in a manner similar to applying a bandage. An adhesive backing may be used to facilitate attachment to the skin. The microneedle array can be supplied to the consumer in a sterile pouch with the microneedle tips capped by a thin layer of epoxy or padding that serves to protect the tips from mishandling. After peeling off this protective layer, the user can then apply the sensing module to the skin surface. The interrogation module can then be attached to the top of the sensing module. The attachment between the sensing module and the interrogation module can be, for example, via clip-on or snap-fit so that the application motion applies only normal force (and no torsional force) to the microneedle array in order to reinforce insertion. However, other attachment mechanisms are also possible, such as, but not limited to, magnetic, luer-lock-style twist attachment, or screw fit. Alternatively or additionally, the sensing module may be coupled to the interrogation module prior to insertion into the skin, in which case the assembled monitoring system can be adhered to the skin.

Thus, embodiments of the disclosed subject matter provide a miniaturized fluorescent light signal detector that allows for an optical instrumentation, which is traditionally large, to be wearable for continuous health parameter tracking. Such small detector may also be ideal for point-of-care diagnostic devices that require measurement of fluorescent light output. Embodiments of the disclosed subject matter can access information internal to the body such as glucose, hormone, and electrolyte level changes using a minimally invasive and low cost platform that accesses the dermal interstitial fluid and continuously measure the concentrations of its contents. The use of microneedles limits tissue damage, reduces the risk of skin infection, and has the potential to be inserted painlessly. Embodiments of the disclosed subject matter are advantageous for those who have diseases that require continuous monitoring (e.g. diabetics and blood sugar, those with blood coagulation disorder and clotting factors, those with a cardiovascular disease and thrombotic factors or infarction factors etc.), as well as the general consumer who may be interested in improving their wellness to prevent the onset of diseases.

Although embodiments have been specifically described above with respect to glucose monitoring, embodiments of the disclosed subject matter are not limited thereto. Other sensors can be embedded into the microneedles for multiple analyte tracking since interstitial fluid also contains, for example, electrolytes, hormones, lactate, urea, amino acids, proteins, enzymes, co-enzymes, and triglycerides.

Embodiments of the disclosed subject matter may enjoy one or more of the following advantages: (1) minimally invasive, (2) compact system, (3) low cost, (4) disposable sensing module and reusable interrogation module, (5) capability for multiplexing, (6) wearable, (7) continuous monitoring.

One or more first embodiments provide an apparatus for determining a concentration of an analyte in a living subject. The apparatus includes at least one microneedle sized and shaped to penetrate a stratum corneum of the subject and access a dermal interstitial fluid layer of the subject. The at least one microneedle comprises a hydrogel material that interfaces with the dermal interstitial fluid layer. The hydrogel material includes a substance that fluoresces in a second wavelength range when illuminated by light in a first wavelength range when the substance interacts with the analyte, wherein a magnitude of the fluorescence varies as a function of the concentration of the analyte. A light source is positioned to illuminate the hydrogel material with illumination light in the first wavelength range while the hydrogel material is interfacing with the dermal interstitial fluid layer. The apparatus also includes a photosensor responsive to light in the second wavelength range that is emitted by the substance while the hydrogel material is interfacing with the dermal interstitial fluid layer. The photosensor generates an output that corresponds to an amount of light received in the second wavelength range.

In the first embodiments or any other embodiment, the at least one microneedle may comprise an unenclosed dried hydrogel material that is sufficiently hard to penetrate a stratum corneum.

In the first embodiments or any other embodiment, the at least one microneedle may comprise a hollow scaffold filled with the hydrogel material.

In the first embodiments or any other embodiment, the apparatus may further include a wavelength selective filter that attenuates light in the first wavelength range and transmits light in the second wavelength range, wherein the wavelength selective filter is disposed in an optical path between the hydrogel material and the photosensor. Optionally, the apparatus further includes an angle-of-incidence filter disposed in the optical path between the hydrogel material and the wavelength selective filter.

In the first embodiments or any other embodiment, the apparatus may further include an amplifier connected to the photosensor to amplify the output of the photosensor and generate an output signal, and a controller that is programmed to determine the concentration of the analyte based on the output signal generated by the amplifier.

In the first embodiments or any other embodiment, the at least one microneedle may be disposed in a first module, the light source and the photosensor are disposed in a second module, and the second module is connected to the first module via a releasable coupling. Optionally, the at least one microneedle comprises at least one pointed tip and at least one back, and the at least one pointed tip is disposed on a bottom of the first module with the at least one pointed tip facing down. The light source and the photosensor are aimed at the at least one back of the at least one microneedle. Optionally, the apparatus further includes an adhesive disposed on the bottom of the first module. Optionally, the at least one microneedle comprises a two-dimensional array of microneedles.

In the first embodiments or any other embodiment, the apparatus may further include a wavelength selective filter that attenuates light in the first wavelength range and transmits light in the second wavelength range, wherein the wavelength selective filter is disposed in an optical path between the hydrogel material and the photosensor. The at least one microneedle comprises a two-dimensional array of microneedles disposed in a first module, wherein each of the microneedles in the array has a pointed tip and a back, and the pointed tip is disposed on a bottom of the first module with the pointed tip facing down. The light source and the photosensor are disposed in a second module, and the second module is connected to the first module via a releasable coupling. The light source and the photosensor are aimed at the back of the microneedles. Optionally, the apparatus further includes an angle-of-incidence filter disposed in the optical path between the hydrogel material and the wavelength selective filter. Optionally, the apparatus further includes an amplifier connected to the photosensor to amplify the output of the photosensor and generate an output signal, and a controller that is programmed to determine the concentration of the analyte based on the output signal generated by the amplifier.

One or more second embodiments provide an apparatus for determining a concentration of an analyte in a living subject. The apparatus includes a plurality of microneedles comprising a hydrogel material that transmits light in a first wavelength range and transmits light in a second wavelength range. The plurality of microneedles are sized and shaped to penetrate a stratum corneum of a live subject and interface the hydrogel material with a dermal interstitial fluid layer of the subject. The apparatus also includes a fluorescent substance disposed in the hydrogel material. The substance fluoresces in the second wavelength range when illuminated by light in the first wavelength range when the substance interacts with the analyte. A magnitude of the fluorescence varies as a function of the concentration of the analyte. The apparatus also includes a photosensor positioned to receive light arriving from the hydrogel material. The photosensor is responsive to light in the second wavelength range that is emitted by the substance while the hydrogel material is interfacing with the dermal interstitial fluid layer. The photosensor generates an output that corresponds to an amount of light received in the second wavelength range. The apparatus also includes a wavelength selective filter disposed in an optical path between the hydrogel material and the photosensor. The wavelength selective filter attenuates light in the first wavelength range and transmits light in the second wavelength range. The apparatus also includes a light source positioned to illuminate the hydrogel material with illumination light in the first wavelength range while the hydrogel material is interfacing with the dermal interstitial fluid layer.

In the second embodiments or any other embodiment, the apparatus may further include an amplifier connected to the photosensor to amplify the output of the photosensor and generate an output signal, and a controller that is programmed to determine the concentration of the analyte based on the output signal generated by the amplifier.

In the first embodiments or any other embodiment, the light source may comprise at least one LED.

In the first embodiments or any other embodiment, the plurality of microneedles may be disposed in a first module, the light source and the photosensor are disposed in a second module, and the second module is connected to the first module via a releasable coupling. Optionally, the plurality of microneedles have pointed tips and backs, and the pointed tips are disposed on a bottom of the first module with the pointed tips facing down, and the light source and the photosensor are aimed at the backs of the plurality of microneedles. Optionally, the apparatus further includes an adhesive disposed on the bottom of the first module. Optionally, the plurality of microneedles comprises a two-dimensional array of microneedles. Optionally, the apparatus further includes an angle-of-incidence filter disposed in the optical path between the hydrogel material and the wavelength selective filter. Optionally, the apparatus further includes an amplifier connected to the photosensor to amplify the output of the photosensor and generate an output signal, and a controller that is programmed to determine the concentration of the analyte based on the output signal generated by the amplifier.

In the second embodiments or any other embodiment, the light source may be disposed between the wavelength selective filter and the hydrogel material, and the illumination from the light source is aimed downward onto the hydrogel material.

In the second embodiments or any other embodiment, the wavelength selective filter may be affixed to a lower surface of the photosensor, the light source is affixed to a lower surface of the wavelength selective filter, and the illumination from the light source is aimed downward onto the hydrogel material.

In the second embodiments or any other embodiment, the apparatus may further include an angle-of-incidence filter disposed in the optical path between the hydrogel material and the wavelength selective filter. Optionally, the wavelength selective filter is affixed to a lower surface of the photosensor, the angle-of-incidence filter is affixed to a lower surface of the wavelength selective filter, the light source is affixed to a lower surface of the angle-of-incidence filter, and the illumination from the light source is aimed downward onto the hydrogel material.

In the second embodiments or any other embodiment, the apparatus may further include at least one optical beam splitter disposed between the hydrogel material and the wavelength selective filter. The at least one optical beam splitter is positioned and oriented to route light in the second wavelength range that is emitted by the substance towards the photosensor, and the at least one optical beam splitter is positioned and oriented to route the illumination light from the light source towards the hydrogel material. Optionally, the illumination light from the light source enters the at least one optical beam splitter from a lateral direction. Optionally, the light source comprises at least one LED.

The at least one optical beam splitter may comprise two optical beam splitters, and the illumination light from the light source enters the two optical beam splitters from two opposing lateral directions. Alternatively, the at least one optical beam splitter comprises four optical beam splitters, and the illumination light from the light source enters the four optical beam splitters from four lateral directions. Optionally, these four optical beam splitters are arranged in a pyramid configuration.

One or more third embodiments provide an apparatus for determining a concentration of an analyte in a living subject. The apparatus includes a hydrogel base having an upper surface and a lower surface, and a plurality of microneedles affixed to the lower surface of the hydrogel base. The plurality of microneedles are made of a dried hydrogel material that transmits light in a first wavelength range and transmits light in a second wavelength range. The plurality of microneedles are sized and shaped to penetrate a stratum corneum of a live subject and access a dermal interstitial fluid layer of the subject. The apparatus also includes a fluorescent substance disposed in the plurality of microneedles, and the substance fluoresces in the second wavelength range when illuminated by light in the first wavelength range when the substance interacts with the analyte. A magnitude of the fluorescence varies as a function of the concentration of the analyte. The apparatus also includes a photosensor disposed above the hydrogel base. The photosensor is responsive to light in the second wavelength range that is emitted by the substance while the plurality of microneedles is accessing the dermal interstitial fluid layer, and the photosensor generates an output that corresponds to an amount of light received in the second wavelength range. The apparatus also includes a wavelength selective filter disposed in an optical path between the plurality of microneedles and the photosensor. The wavelength selective filter attenuates light in the first wavelength range and transmits light in the second wavelength range. The apparatus also includes a light source positioned to illuminate the plurality of microneedles with illumination light in the first wavelength range while the plurality of microneedles is accessing the dermal interstitial fluid layer.

In the third embodiments or any other embodiment, the apparatus may further include an amplifier connected to the photosensor to amplify the output of the photosensor and generate an output signal, and a controller that is programmed to determine the concentration of the analyte based on the output signal generated by the amplifier.

In the third embodiments or any other embodiment, the hydrogel base may have a concave upper surface.

In the third embodiments or any other embodiment, the light source may comprise at least one LED.

In the third embodiments or any other embodiment, the plurality of microneedles may be disposed in a first module, the light source and the photosensor are disposed in a second module, and the second module is connected to the first module via a releasable coupling. Optionally, the plurality of microneedles comprises a plurality of pointed tips and a plurality of backs, and the plurality of pointed tips is disposed on a bottom of the first module with the plurality of pointed tips facing down. The light source and the photosensor are aimed at the plurality of backs of the plurality of microneedles. Optionally, the apparatus further includes an adhesive disposed on the bottom of the first module. Optionally, the plurality of microneedles comprises a two-dimensional array of microneedles.

In the third embodiments or any other embodiment, the photosensor that is disposed above the hydrogel base may be disposed less than 2 cm above the hydrogel base.

In the third embodiments or any other embodiment, the light source may be disposed between the wavelength selective filter and the hydrogel base, and the illumination from the light source is aimed downward onto the hydrogel base.

In the third embodiments or any other embodiment, the wavelength selective filter may be affixed to a lower surface of the photosensor, the light source is affixed to a lower surface of the wavelength selective filter, and the illumination from the light source is aimed downward onto the hydrogel base. Optionally, the hydrogel base has a concave upper surface.

In the third embodiments or any other embodiment, the apparatus may further include an angle-of-incidence filter disposed in the optical path between the plurality of microneedles and the wavelength selective filter. Optionally, the wavelength selective filter is affixed to a lower surface of the photosensor, the angle-of-incidence filter is affixed to a lower surface of the wavelength selective filter, the light source is affixed to a lower surface of the angle-of-incidence filter, and the illumination from the light source is aimed downward onto the hydrogel base. Optionally, the hydrogel base has a concave upper surface.

In the third embodiments or any other embodiment, the apparatus may further include at least one optical beam splitter disposed between the hydrogel base and the wavelength selective filter. The at least one optical beam splitter is positioned and oriented to route light in the second wavelength range that is emitted by the substance towards the photosensor, and the at least one optical beam splitter is positioned and oriented to route the illumination light from the light source towards the plurality of microneedles. Optionally, the illumination light from the light source enters the at least one optical beam splitter from a lateral direction. Optionally, the light source comprises at least one LED. Optionally, the hydrogel base has a concave upper surface.

The at least one optical beam splitter may comprise two optical beam splitters, and the illumination light from the light source enters the two optical beam splitters from two opposing lateral directions. Alternatively, the at least one optical beam splitter comprises four optical beam splitters, and the illumination light from the light source enters the four optical beam splitters from four lateral directions. Optionally, these four optical beam splitters are arranged in a pyramid configuration.

In the third embodiments or any other embodiment, the hydrogel base may have a lateral outer boundary, and the light source is mounted laterally beyond the lateral outer boundary of the hydrogel base.

One or more fourth embodiments provide an apparatus including a microneedle and a fluorescent substance disposed in the microneedle. The microneedle is made of a dried hydrogel material that transmits light in a first wavelength range and transmits light in a second wavelength range. The microneedle is sized and shaped to penetrate a stratum corneum of a live subject and access a dermal interstitial fluid layer of the subject, and the dried hydrogel material is formed by drying a hydrated hydrogel material having a shrinkage percentage of less than 30%. The fluorescent substance fluoresces in the second wavelength range when illuminated by light in the first wavelength range when the substance interacts with an analyte. A magnitude of the fluorescence varies as a function of a concentration of the analyte.

In the fourth embodiments or any other embodiment, the dried hydrogel material may comprise poly(2-hydroxyethyl methacrylate).

In the fourth embodiments or any other embodiment, the dried hydrogel material may comprise a dried polyacrylamide hydrogel.

In the fourth embodiments or any other embodiment, the dried hydrogel material may comprise a polyacrylamide hydrogel having a high percentage of AAm and a low AAm/MBAm ratio. The polyacrylamide hydrogel may have an AAm percentage between 28 and 32 and an AAm/MBAm ratio between 14 and 16. The polyacrylamide hydrogel may have an AAm percentage between 29 and 31 and an AAm/MBAm ratio between 14.5 and 15.5.

In the fourth embodiments or any other embodiment, the microneedle may be formed by immersing a needle-shaped hydrated hydrogel in a bath of ethanol and subsequently drying the needle-shaped hydrated hydrogel.

In the fourth embodiments or any other embodiment, the microneedle is formed by immersing a hydrated needle-shaped polyacrylamide hydrogel in a bath of ethanol and subsequently drying the hydrated needle-shaped polyacrylamide hydrogel.

One or more fifth embodiments provide an apparatus that includes a hydrogel base having an upper surface and a lower surface, and a plurality of microneedles affixed to the lower surface of the hydrogel base. The plurality of microneedles are made of a dried hydrogel material that transmits light in a first wavelength range and transmits light in a second wavelength range, and the plurality of microneedles are sized and shaped to penetrate a stratum corneum of a live subject and access a dermal interstitial fluid layer of the subject. A fluorescent substance is disposed in the plurality of microneedles, and the substance fluoresces in the second wavelength range when illuminated by light in the first wavelength range when the substance interacts with an analyte. A magnitude of the fluorescence varies as a function of a concentration of the analyte.

In the fifth embodiments or any other embodiment, the upper surface of the hydrogel base may be concave. The concave shape of the upper surface of the hydrogel base may be shaped to focus light in the second wavelength range onto a photosensor.

In the fifth embodiments or any other embodiment, the fluorescent substance may not be incorporated into the hydrogel base.

In the fifth embodiments or any other embodiment, the plurality of microneedles may comprise at least four microneedles.

In the fifth embodiments or any other embodiment, the plurality of microneedles may comprise a 3×3 array of microneedles.

In the fifth embodiments or any other embodiment, the plurality of microneedles may have diameters between 175 and 225 µm and lengths between 1300 and 1500 µm.

In the fifth embodiments or any other embodiment, the apparatus may be formed using a mold that has a lower portion with a plurality of needle-shaped wells and an upper portion that forms a base for the plurality of microneedles. The apparatus is formed by filling the plurality of needle shaped wells with a mixture of hydrogel and the fluorescent substance, and subsequently filling the upper portion of the mold with hydrogel, so as to form a hydrated hydrogel base with a plurality of hydrated microneedles affixed to the base. Optionally, the apparatus is formed by immersing the hydrated hydrogel base with the plurality of hydrated microneedles affixed to the base in a bath of ethanol and subsequently drying the hydrated hydrogel base with the plurality of hydrated microneedles affixed to the base.

In the fifth embodiments or any other embodiment, the dried hydrogel material may be formed by drying a hydrated hydrogel material having a shrinkage percentage of less than 30%.

In the fifth embodiments or any other embodiment, the dried hydrogel material may comprise a polyacrylamide hydrogel having a high percentage of AAm and a low AAm/MBAm ratio. Optionally, the polyacrylamide hydrogel has an AAm percentage between 28 and 32 and an AAm/MBAm ratio between 14 and 16. Optionally, the polyacrylamide hydrogel has an AAm percentage between 29 and 31 and an AAm/MBAm ratio between 14.5 and 15.5.

One or more sixth embodiments provide a method of fabricating an array of hydrogel microneedles affixed to a base. The method includes adding a fluorescent substance to a first quantity of hydrogel material, wherein the substance fluoresces in a second wavelength range when illuminated by light in a first wavelength range when the substance interacts with an analyte. A magnitude of the fluorescence varies as a function of a concentration of the analyte. The method also includes introducing the first quantity of hydrogel material with the added fluorescent substance into a plurality of needle shaped wells located at a bottom of a mold, and introducing a second quantity of hydrogel material into an upper portion of the mold above the first quantity of hydrogel material disposed in the needle shaped wells. The second quantity of hydrogel material forms a base for the first quantity of hydrogel material disposed in the needle shaped wells. The method also includes removing the first quantity of hydrogel material and the second quantity of hydrogel material from the mold, and drying the first quantity of hydrogel material and the second quantity of hydrogel material. The dried first quantity of hydrogel material and the dried second quantity of hydrogel material transmit light in the first wavelength range and transmit light in the second wavelength range.

In the sixth embodiments or any other embodiment, the method may further include shaping a top of the second quantity of hydrogel material to have a concave shape.

In the sixth embodiments or any other embodiment, the fluorescent substance may not be incorporated into the second quantity of hydrogel material.

In the sixth embodiments or any other embodiment, the plurality of needle shaped wells may comprise at least four needle shaped wells.

In the sixth embodiments or any other embodiment, the plurality of needle shaped wells may comprise a 3×3 array of needle shaped wells.

In the sixth embodiments or any other embodiment, the plurality of needle shaped wells may have diameters between 175 and 225 µm and lengths between 1300 and 1500 µm.

In the sixth embodiments or any other embodiment, the method may further include immersing the first quantity of hydrogel material and the second quantity of hydrogel material in a bath of ethanol after removing and prior to drying.

In the sixth embodiments or any other embodiment, the first quantity of hydrogel material and the second quantity of hydrogel material may have a shrinkage percentage of less than 30%.

In the sixth embodiments or any other embodiment, the first quantity of hydrogel material and the second quantity of hydrogel material may comprise a polyacrylamide hydrogel having a high percentage of AAm and a low AAm/MBAm ratio. Optionally, the polyacrylamide hydrogel has an AAm percentage between 28 and 32 and an AAm/MBAm ratio between 14 and 16. Optionally, the method further includes immersing the first quantity of hydrogel material and the second quantity of hydrogel material in a bath of ethanol after removing and prior to drying.

In the sixth embodiments or any other embodiment, the first quantity of hydrogel material and the second quantity of hydrogel material may comprise a polyacrylamide hydrogel having an AAm percentage between 29 and 31 and an AAm/MBAm ratio between 14.5 and 15.5 and the method further includes immersing the first quantity of hydrogel material and the second quantity of hydrogel material in a bath of ethanol after removing and prior to drying.

One or more seventh embodiments provide a system for monitoring a chemical in the body of a user comprises a sensing module and interrogation module. The sensing module includes one or more microneedles and a hydrogel responsive to the chemical in the body. The hydrogel can fluoresce in response to excitation light. The interrogation module includes a light source, a light detector, and one or more optical components. The light source generates the excitation light, while the light detector detects the fluorescence from the hydrogel. The one or more optical components separate the excitation light from the fluorescence.

In the seventh embodiments or any other embodiment, the chemical may be one of glucose, electrolytes, hormones, lactate, urea, amino acids, proteins, enzymes, co-enzymes, triglycerides, and cholesterol.

In the seventh embodiments or any other embodiment, the chemical may be glucose and hydrogel comprises a glucose-responsive dye conjugated to poly(2-hydroxyethyl methacrylate) or polyacrylamide hydrogel.

In the seventh embodiments or any other embodiment, the hydrogel responsive to said chemical may fill an interior volume of each microneedle from the tip to an interior volume of the sensing module.

In the seventh embodiments or any other embodiment, the hydrogel responsive to said chemical may form at least the tip of each microneedle.

In the seventh embodiments or any other embodiment, each microneedle may comprise a waveguide to convey light to and from the hydrogel responsive to said chemical. Optionally, the waveguide is a multimode optical fiber.

In the seventh embodiments or any other embodiment, the interrogation module may be releasably coupled to the sensing module so as to be reusable with a different sensing module.

In the seventh embodiments or any other embodiment, the coupling may comprise a snap-fit or clip-on configuration.

In the seventh embodiments or any other embodiment, the interrogation module is constructed to be coupled to the sensing module after insertion of the one or more microneedles into the skin of the user.

In the seventh embodiments or any other embodiment, the interrogation module is constructed such that most of a force of the coupling is in a direction of the insertion.

In the seventh embodiments or any other embodiment, each microneedle is sized to penetrate the stratum corneum to access the dermal interstitial fluid without reaching the capillary bed when the sensing module is attached to the skin of the user.

In the seventh embodiments or any other embodiment, the interrogation module comprises a power supply for the light source and the light detector.

In the seventh embodiments or any other embodiment, the interrogation module comprises a processor connected to the light source and the light detector to control operation thereof, the processor being configured to process signals from the light detector to determine a property of said chemical.

In the seventh embodiments or any other embodiment, the interrogation module comprises a temperature sensor, and the processor is configured to determine the property of said chemical responsively to a signal from the temperature sensor.

In the seventh embodiments or any other embodiment, the temperature sensor comprises a plurality of temperature sensors, at least one of the plurality measuring a temperature of the light detector and/or the hydrogel, and at least another of the plurality measuring a temperature of the skin of the user or a temperature of the system.

In the seventh embodiments or any other embodiment, the temperature sensor comprises a printed platinum resistor, a thermocouple, a thermistor, a resistance temperature detector, or an infrared sensor.

In the seventh embodiments or any other embodiment, the temperature sensor measures a temperature of the light detector and/or the hydrogel.

In the seventh embodiments or any other embodiment, the light source, the light detector, and the one or more optical components are arranged in a stack in a direction parallel to an axis of the one or more microneedles, and the optical components comprise at least a wavelength filter that prevents passage of the excitation light therethrough.

In the seventh embodiments or any other embodiment, the at least a wavelength filter comprises an ultra-violet (UV) filter and an angle of incidence (AOI) filter, the UV filter being between the light detector and the AOI filter, and the AOI filter being between the UV filter and the light source.

In the seventh embodiments or any other embodiment, the light source has a surface area that is less than a detection area of the light detector.

In the seventh embodiments or any other embodiment, the light source is transparent to the fluorescence light.

In the seventh embodiments or any other embodiment, the light source comprises one or more light-emitting diodes (LEDs).

In the seventh embodiments or any other embodiment, the light detector comprises a single light detector or multiple light detectors.

In the seventh embodiments or any other embodiment, the light detector is one of a photodiode and a CCD camera.

In the seventh embodiments or any other embodiment, at least the interrogation module includes a housing with thermal insulation, the housing being constructed to seal with the sensing module to prevent exterior light from entering the housing and to minimize thermal changes to the light detector.

In the seventh embodiments or any other embodiment, the interrogation module further comprises an active thermal management unit that regulates a temperature of at least the light detector.

In the seventh embodiments or any other embodiment, the light detector is thermally isolated from other components of the interrogation module.

In the seventh embodiments or any other embodiment, the light source, the light detector, and the one or more optical components are spaced from each other, the optical components comprise at least a beam splitter.

In the seventh embodiments or any other embodiment, the beam splitter is a dichroic or dielectric mirror.

In the seventh embodiments or any other embodiment, the light source comprises at least two LEDs arranged on a periphery of the interrogation module, a corresponding number of beam splitters centered between the at least two LEDs, and the light detector centered between the at least two LEDs so as to receive fluorescence passing through the beam splitters.

In the seventh embodiments or any other embodiment, a maximum width of the system is less than or equal to 20 mm, and a height from a surface of the skin of less than or equal to 25 mm.

In the seventh embodiments or any other embodiment, the illumination of the hydrogel with excitation light from the light source is periodic, for example, on the order of milliseconds.

In this application, unless specifically stated otherwise, the use of the singular includes the plural and the use of "or" means "and/or." Furthermore, use of the terms "including" or "having," as well as other forms, such as "includes," "included," "has," or "had" is not limiting. Any range described herein will be understood to include the endpoints and all values between the endpoints. Moreover, any use of terms such as "near," "approximate," or the like, include the recited limitation as well as values within 10% of the recited limitation.

Furthermore, the foregoing descriptions apply, in some cases, to examples generated in a laboratory, but these examples can be extended to production techniques. For example, where quantities and techniques apply to the laboratory examples, they should not be understood as limiting. In addition, although specific chemicals and materials have been disclosed herein, other chemicals and materials may also be employed according to one or more contemplated embodiments.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, system, methods, and devices for health parameter tracking and/or point-of-care diagnostics. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicants intend to embrace all such alternatives, modifications, equivalents, and variations that are within the spirit and scope of the present invention.

What is claimed is:

1. An apparatus comprising:
    a microneedle made of a dried hydrogel material that transmits light in a first wavelength range and transmits light in a second wavelength range, wherein the microneedle is sized and shaped to penetrate a stratum corneum of a live subject and access a dermal interstitial fluid layer of the subject, and wherein the dried hydrogel material is formed by drying a hydrated hydrogel material having a shrinkage percentage of less than 30%; and
    a fluorescent substance disposed in the microneedle, wherein the substance fluoresces in the second wavelength range when illuminated by light in the first wavelength range when the substance interacts with an analyte, wherein a magnitude of the fluorescence varies as a function of a concentration of the analyte.

2. The apparatus of claim 1, wherein the dried hydrogel material comprises poly(2-hydroxyethyl methacrylate).

3. The apparatus of claim 1, wherein the dried hydrogel material comprises a dried polyacrylamide hydrogel.

4. The apparatus of claim 1, wherein the dried hydrogel material comprises a polyacrylamide hydrogel having a high percentage of AAm and a low AAm/MBAm ratio.

5. The apparatus of claim 4, wherein the polyacrylamide hydrogel has an AAm percentage between 28 and 32 and an AAm/MBAm ratio between 14 and 16.

6. The apparatus of claim 4, wherein the polyacrylamide hydrogel has an AAm percentage between 29 and 31 and an AAm/MBAm ratio between 14.5 and 15.5.

7. An apparatus comprising:
    a hydrogel base having an upper surface and a lower surface;
    a plurality of microneedles affixed to the lower surface of the hydrogel base, wherein the plurality of microneedles are made of a dried hydrogel material that transmits light in a first wavelength range and transmits light in a second wavelength range, and wherein the plurality of microneedles are sized and shaped to penetrate a stratum corneum of a live subject and access a dermal interstitial fluid layer of the subject; and
    a fluorescent substance disposed in the plurality of microneedles, wherein the substance fluoresces in the second wavelength range when illuminated by light in the first wavelength range when the substance interacts with an analyte, wherein a magnitude of the fluorescence varies as a function of a concentration of the analyte.

8. The apparatus of claim 7, wherein the upper surface of the hydrogel base is concave.

9. The apparatus of claim 8, wherein the concave shape of the upper surface of the hydrogel base is shaped to focus light in the second wavelength range onto a photosensor.

10. The apparatus of claim 7, wherein the fluorescent substance is not incorporated into the hydrogel base.

11. The apparatus of claim 7, wherein the plurality of microneedles have diameters between 175 and 225 μm and lengths between 1300 and 1500 μm.

12. The apparatus of claim 7, wherein the dried hydrogel material comprises a polyacrylamide hydrogel having a high percentage of AAm and a low AAm/MBAm ratio.

13. The apparatus of claim 12, wherein the polyacrylamide hydrogel has an AAm percentage between 28 and 32 and an AAm/MBAm ratio between 14 and 16.

14. The apparatus of claim 12, wherein the polyacrylamide hydrogel has an AAm percentage between 29 and 31 and an AAm/MBAm ratio between 14.5 and 15.5.

15. A method of fabricating an array of hydrogel microneedles affixed to a base, the method comprising:
    adding a fluorescent substance to a first quantity of hydrogel material, wherein the substance fluoresces in a second wavelength range when illuminated by light in a first wavelength range when the substance interacts with an analyte, wherein a magnitude of the fluorescence varies as a function of a concentration of the analyte;
    introducing the first quantity of hydrogel material with the added fluorescent substance into a plurality of needle shaped wells located at a bottom of a mold;
    introducing a second quantity of hydrogel material into an upper portion of the mold above the first quantity of hydrogel material disposed in the needle shaped wells, wherein the second quantity of hydrogel material forms a base for the first quantity of hydrogel material disposed in the needle shaped wells;
    removing the first quantity of hydrogel material and the second quantity of hydrogel material from the mold; and
    drying the first quantity of hydrogel material and the second quantity of hydrogel material,
    wherein the dried first quantity of hydrogel material and the dried second quantity of hydrogel material transmit light in the first wavelength range and transmit light in the second wavelength range.

16. The method of claim 15, wherein the fluorescent substance is not incorporated into the second quantity of hydrogel material.

17. The method of claim 15, wherein the plurality of needle shaped wells have diameters between 175 and 225 μm and lengths between 1300 and 1500 μm.

18. The method of claim 15, further comprising immersing the first quantity of hydrogel material and the second quantity of hydrogel material in a bath of ethanol after removing and prior to drying.

19. The method of claim 15, wherein the first quantity of hydrogel material and the second quantity of hydrogel material have a shrinkage percentage of less than 30%.

20. The method of claim 15, wherein the first quantity of hydrogel material and the second quantity of hydrogel material comprise a polyacrylamide hydrogel having an AAm percentage between 28 and 32 and an AAm/MBAm ratio between 14 and 16.

21. The method of claim 20, further comprising immersing the first quantity of hydrogel material and the second quantity of hydrogel material in a bath of ethanol after removing and prior to drying.

22. The method of claim 21, wherein the polyacrylamide hydrogel has an AAm percentage between 29 and 31 and an AAm/MBAm ratio between 14.5 and 15.5.

* * * * *